US010369109B2

(12) United States Patent
Bartholomaeus et al.

(10) Patent No.: US 10,369,109 B2
(45) Date of Patent: *Aug. 6, 2019

(54) ABUSE-PROOFED DOSAGE FORM

(71) Applicant: GRÜNENTHAL GMBH, Aachen (DE)

(72) Inventors: Johannes Bartholomaeus, Aachen (DE); Heinrich Kugelmann, Aachen (DE)

(73) Assignee: GRÜNENTHAL GMBH, Aachen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/032,533

(22) Filed: Jul. 11, 2018

(65) Prior Publication Data
US 2018/0318223 A1 Nov. 8, 2018

Related U.S. Application Data

(63) Continuation of application No. 15/587,501, filed on May 5, 2017, now abandoned, which is a continuation of application No. 15/245,424, filed on Aug. 24, 2016, now Pat. No. 9,675,610, which is a continuation of application No. 14/527,911, filed on Oct. 30, 2014, now abandoned, which is a continuation of application No. 14/069,439, filed on Nov. 1, 2013, now abandoned, which is a continuation of application No. 13/803,789, filed on Mar. 14, 2013, now abandoned, which is a continuation of application No. 13/572,926, filed on Aug. 13, 2012, now abandoned, which is a continuation of application No. 13/365,742, filed on Feb. 3, 2012, now abandoned, which is a continuation of application No. 12/822,719, filed on Jun. 24, 2010, now abandoned, which is a continuation of application No. 11/007,887, filed on Dec. 9, 2004, now Pat. No. 7,776,314, which is a continuation of application No. PCT/EP03/06314, filed on Jun. 16, 2003.

(30) Foreign Application Priority Data

Jun. 17, 2002 (DE) .................................. 102 27 077
Oct. 25, 2002 (DE) .................................. 102 50 083

(51) Int. Cl.
A61K 31/485 (2006.01)
A61K 9/20 (2006.01)
A61K 9/48 (2006.01)
A61K 31/137 (2006.01)
A61K 31/5513 (2006.01)
A61K 45/06 (2006.01)
A61K 47/38 (2006.01)
A61K 9/00 (2006.01)

(52) U.S. Cl.
CPC .......... A61K 9/2054 (2013.01); A61K 9/0053 (2013.01); A61K 9/205 (2013.01); A61K 9/2009 (2013.01); A61K 9/2013 (2013.01); A61K 9/4866 (2013.01); A61K 31/137 (2013.01); A61K 31/485 (2013.01); A61K 31/5513 (2013.01); A61K 45/06 (2013.01); A61K 47/38 (2013.01)

(58) Field of Classification Search
None
See application file for complete search history.

(56) References Cited

U.S. PATENT DOCUMENTS

| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,658,259 A | 4/1972 | Ledergerber et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |

(Continued)

FOREIGN PATENT DOCUMENTS

| AR | 046994 A1 | 12/2004 |
| AR | 045353 A1 | 10/2005 |

(Continued)

OTHER PUBLICATIONS 2.9 Methoden der pharmazeutischen Technologie, European Pharmacopeia, 143-144, 1997, (Full English translation attached).
Albertini, B. "New spray congealing atomizer for the microencapsulation of highly concentrated solid and liquid substances" European Journal of Pharmaceutics and Biopharmaceutics 69 (2008) 348-357.
Alekseeva et al, Chemical-Pharmaceutical Journal, vol. 41, No. 9, 2007, 49-52. (Full translation attached.).
Almeida, A. et al., Ethylene vinyl acetate as matrix for oral sustained release dosage forms produced via hot-melt extrusion, European Journal of Pharmaceutics and Biopharmaceutics 77 (2011) 297-305.

(Continued)

Primary Examiner — Jessica Worsham
(74) Attorney, Agent, or Firm — Norris McLaughlin, P.A.

(57) ABSTRACT

A solid administration form, protected from parenteral abuse and containing at least one viscosity-increasing agent in addition to one or more active substances that have parenteral abuse potential. The agent forms, when a necessary minimum amount of an aqueous liquid is added, on the basis of an extract obtained from the administration form, a preferably injectable gel that remains visually distinct when introduced into another quantity of an aqueous liquid.

28 Claims, No Drawings

(56) References Cited

U.S. PATENT DOCUMENTS

| | | |
|---|---|---|
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,384,020 B1 | 5/2002 | Flanner et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |

(56) References Cited

U.S. PATENT DOCUMENTS

| | | |
|---|---|---|
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,157,103 B2 | 11/2007 | Sackler |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Bartholomaeus et al. |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 9,855,263 B2 | 1/2018 | Wening et al. |
| 9,884,022 B2 | 2/2018 | Deshmukh et al. |
| 9,925,146 B2 | 3/2018 | Barnscheid et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0079138 A1 | 4/2005 | Chickering, III et al. |
| 2005/0089475 A1 | 4/2005 | Gruber |
| 2005/0089569 A1 | 4/2005 | Bar-Shalom |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0095291 A1 | 8/2005 | Oshlack et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaeus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaeus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |

(56) References Cited

U.S. PATENT DOCUMENTS

| | | |
|---|---|---|
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1 | 3/2007 | Chastain et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannionl et al. |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0014228 A1 | 1/2008 | Darmuzey et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 4/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1 | 6/2009 | Richardson et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0258066 A1 | 10/2009 | Venkatesh et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0028972 A1 | 1/2013 | Schwier et al. |
| 2013/0059010 A1 | 3/2013 | Henry et al. |
| 2013/0090349 A1 | 4/2013 | Barnscheid et al. |
| 2013/0129825 A1 | 5/2013 | Billoet et al. |
| 2013/0129826 A1 | 5/2013 | Barnscheid et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomaus et al. |
| 2013/0289062 A1 | 10/2013 | Kumar et al. |
| 2013/0001726 A1 | 11/2013 | Mullen et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0034885 A1 | 2/2014 | Leech |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0190348 A1 | 7/2015 | Haksar et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |

(56) References Cited

U.S. PATENT DOCUMENTS

| | | | |
|---|---|---|---|
| 2016/0361308 A1 | 12/2016 | Bartholomaeus et al. | |
| 2016/0367549 A1 | 12/2016 | Bartholomaeus et al. | |
| 2017/0027886 A1 | 2/2017 | Bartholomaeus et al. | |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | P10413318 A | 10/2006 |
| BR | P10413361 A | 10/2006 |
| BR | P10513300 A | 5/2008 |
| BR | P10606145 A2 | 2/2009 |
| CA | 0722109 A | 11/1965 |
| CA | 2082573 C | 5/1993 |
| CA | 2577233 A1 | 10/1997 |
| CA | 26505637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1967 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0277289 B1 | 4/1969 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |

(56) References Cited

FOREIGN PATENT DOCUMENTS

| | | |
|---|---|---|
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 S1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1813276 A1 | 8/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 1/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070272 T3 | 11/2007 |
| HR | 20070456 T3 | 11/2007 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2000513333 A | 10/2000 |
| JP | 2002524150 A | 8/2002 |
| JP | 2002-275175 A | 9/2002 |
| JP | 2003113119 A | 4/2003 |
| JP | 2003125706 A | 5/2003 |
| JP | 2003526598 A | 9/2003 |
| JP | 2004143071 A | 5/2004 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009524626 A | 7/2009 |
| JP | 2009531453 A | 9/2009 |
| JP | 2009536927 A | 10/2009 |
| JP | 2009537456 A | 10/2009 |
| JP | 2010527285 A | 8/2010 |
| JP | 2010534204 A | 11/2010 |
| JP | 2011504455 A | 2/2011 |
| JP | 2011506493 A | 3/2011 |
| JP | 2011510034 A | 3/2011 |
| JP | 2013536810 A | 3/2011 |
| JP | 2012515735 A | 7/2012 |
| JP | 2012528845 A | 11/2012 |
| JP | 2013523804 A | 6/2013 |
| JP | 2013155124 A | 8/2013 |
| JP | 2014505736 A | 3/2014 |
| JP | 2014528437 A | 10/2014 |
| JP | 6085307 B2 | 2/2017 |
| JP | 2013523780 A | 6/2017 |
| KR | 1020060069832 | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |

(56) References Cited

FOREIGN PATENT DOCUMENTS

| | | |
|---|---|---|
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 00/15261 A1 | 3/2000 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/068392 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026280 A2 | 4/2004 |
| WO | WO 20047025263 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128417 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |

(56) References Cited

FOREIGN PATENT DOCUMENTS

| | | |
|---|---|---|
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010/0047370 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/059074 A1 | 5/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/025449 A1 | 3/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/048597 A1 | 4/2015 |
| WO | WO 2015/103379 A1 | 7/2015 |
| WO | WO 2015/120201 A1 | 8/2015 |
| WO | WO 2017/178658 A1 | 10/2017 |

OTHER PUBLICATIONS

Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90,1993.
Application of a modelling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., "Catalytic Hydrogenation of a, B-Unsaturated Ketones. III The-Effect of Quantity and Type of Catalysts," J.Org Chem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bannwarth, Bernard, "Will Abuse-Deterrent Formulations of Opioid Analgesics be Successful in Achieving Their Purpose?", Drugs, 2012, vol. 72, pp. 1713-1723.
Bauer et al. Lehrbuch der Pharmazeutischen Technologie. Eight Edition 2006. Stuttgart, pp. 343-352.
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Bingwen et al, 2008, p. 367. (full translation attached).
Block, Lawrence. Medicated Applications. Chapter 88. In Remington's Pharmaceutical Sciences, 17th Ed. 1985.
Borquist et al., "Simulation of the release from a multiparticulate system validated by single pellet and dose release experiements," J. Controlled Release 97: 453-465 (2004).
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.

(56) References Cited

OTHER PUBLICATIONS

Committee for Proprietary Medicinal Products. Note for Guidance on the Investigation of Bioavailability and Bioequivalence. 2001. pp. 1-18.
Compap 90 technical data sheet Mar. 2014; 1 page.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Cuesov, Drug Production Technology, Khar'kov, 1999, pp. 351-352. (Full translation attached.).
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (Abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciemres, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, Polyox WSR Solid Dosage Formulation via Melt Extrusion, Feb. 2003, pp. 1-3.
Efentakis et al, Effects of Excipients on Swelling and Drug Release from Compressed Matrices, in Drug Development and Industrial Pharmacy 23(1):107-112, Jan. 1997, Abstract.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708. 1-1219, dated Sep. 24, 2012.
European Search Report and Opinion Application No. 14176277. 3-1460, dated Dec. 15, 2014.
European Search Report and Opinion, Application No. 11006253. 6-2112, dated Dec. 16, 2011.
European Search Report and Opinion, Application No. 11006254. 4-2112, dated Dec. 16, 2011.
European Search Report and Opinion, Application No. 11008131. 2-1219, dated Feb. 24, 2012.
European Search Report and Opinion, Application No. 11009129. 5-2112, dated Apr. 10, 2012.
European Search Report and Opinion, Application No. 12001296. 8-1219, dated Jun. 26, 2012.
European Search Report and Opinion, Application No. 12001301. 6-1219, dated Jun. 26, 2012.
European Search Report and Opinion, Application No. 12003743. 7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).

(56) References Cited

OTHER PUBLICATIONS

Extended European Search Report for Application No. EP 16182124.4-1455, dated Jan. 17, 2017.
Extended European Search Report for Application No. EP 16183922.0-1460, dated Oct. 31, 2016.
Extended European Search Report and Opinion for Application No. EP 15153679.4-1466, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15184634.2-1455, dated Mar. 3, 2016.
Fathima, N. et al. "Drug-excipient interaction and its importance in dosage form development," Journal of Applied Pharmaceutical Science 01 (06); 2011, pp. 66-71.
Fell J.T., et al, "Determinination of Tablet Strength by the Diametral-Compression Test" Journal of Pharmaceutical Sciences, vol. 59. No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Furu et al. "use of ADHD drugs in the Nordic countries: a population-based comparison study," Acta psychiatrica Scandinavia, May 2010.
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.

Handbook of Pharmaceutical Excipients, 1986, American Pharmaceutical Association, Washington, DC and London (Table of Content Only).
Handbuch der Kunststoff-Extrusionstechnick 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, 16$^{th}$ Edition.
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Koziolek, M. et al., "Development of a bio-relevanf dissolution test device simulating mechanical aspects present in the fed stomach," European Journal of Pharmaceutical Sciences 57 (2014) 250-256.
Lee, Y.-S. et al., Principles of Terahertz Science and Technology (Lecture Notes in Physics), Springer; 1 edition 2008. (Table of Contents Only).
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.

(56) References Cited

OTHER PUBLICATIONS

Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L. et al, "High molecular weight polyethylene oxides (PEOs) as an alternative to HPMC in controlled release dosage form", 2000, International Journal of Pharmaceutics, 195 pp, 229-238.
Maggi, C.. Therapeutic Potential of Capsaicin-like Molecules, Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI, 1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Monolithic: retrieved from internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.

Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta/\9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Nickerson, B., Sample Preparation of Pharmaceutical Dosage Forms, Springer, New York (2011); Chapter-1, pp. 3-48.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.
Oxycodon (Oxygesic): Missbrauch, Abhaengigkeit and toedliche Folgen durch Injection zerstossener Retardtabletten, Deutsphps Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000, pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010,
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT internationai Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 22, 2015.
PCT International Search Report and Written Opinion for PCT Application No. PCT/EP2017/070396 dated Sep. 8, 2017.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.

(56) References Cited

OTHER PUBLICATIONS

Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Oct. 1991, 8(10), S-192.
Pharm. Research, Official Journal of the American Association of Pharmaceutical Scientists, Sep. 1989, 6(9), S-98.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (DOW Mar. 2002); see http://msdssearch.dow.com/PublishedLiteratureDOWCOM/dh_0031/0901b80380031a4a.pdf?filepath=/326-00001.pdf&fromPage=GetDoc).
Polyox Water-Soluble Resins in Pharmaceutical Applications. Dow Chemicals. Published 2004.
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, Chapter 45, pp. 996-1035. (2000) (Full Translation Attached) [76 Examiner rewrote as Rudnic et al, Remington Farmacia, Medica Panamencana, Cpt. 45, pp. 996-1035 (2003).
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka, "Pharmaceutical applications of hot-melt extrusion," MA, Drug Dev Ind Pharm. Oct. 2007; 33(10):1043. (Abstract).

Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58 No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002 Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings— Importance for formulation parameters" European Journal of Pharmaceutics and Biopharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Saleem et al. "Formulation and Evaluation of Tramadol hydrochloride Rectal Suppositories," Indian J. Pharm Sci. Sep.-Oct. 2008; 70(5), 640-644.
Salomies et al., "Determination of Oxycodone Hydrochloride in Oral Solutions by High-Performance Thin-Layer Chromatography/Densitometry," Journal of AOAC International, 83: 1497-1501 (2000).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sax et ai., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schilling, et al., "Novel application of hot-melt extrusion for the preparation of monolithic matrices containing enteric-coated particles." International Journal of Pharmaceutics 400 (2010) 34-31.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks" Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of diastereomeric 3-Dialkylaminopropanols and O-Derivatives., J.f. prakt, Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.

(56) References Cited

OTHER PUBLICATIONS

Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford j., überzogene feste Formen, 1991, 347-68. (English translation attached).
Starch 1500, Partially Pregelatinized Maize Starch, technical data from Colorcon, Feb. 2016, 6 pages.
Strang, Abuse of buprenorphie (Temgesic) by snorting, Letter to the editor, British Med. J., 302: 969 (1991).
Stringer J. L., et al "Diffusion of small molecular weight drugs in radiation-crosslinked poly(ethyleneoxide) hydroqels", Journal of Controlled Release 42, pp, 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen" pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
USP Expert Council, US Pharmacopoeia, Chapter 1092, 2007, 1-15.
Varma et al, Factors Affecting Mechanism and Kinetics of Drug Release from Matrix-Based Oral Controlled Drug Delively Systems, Am. J. Drug Deliv. 2004: 2 (1): 43-57.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vippagunta et al. Crystalline Solids, Advanced Drug Delivery Review 48 (2001), 3-26.
Vynckier et al.,"Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
West, Anthony R., Solid state chemistry and its applications, Wiley, New York, 1988, pp. 358 and 365.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.

(56) References Cited

OTHER PUBLICATIONS

Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1):35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Definition Granule, Merriam-Webster, accessed online Jun. 28, 2018 (2018).
M. Xu et al., "Evaluation of the coat quality of sustained release pellets by individual pellet dissolution methodology," Int. J. Pharm. 478 (2015) 318-327.
PCT International Search Report and Written Opinion for PCT Application No. PCT/EP2016/052046 dated Apr. 12, 2016.
Agarwal, G, et al, "Oral Sustained Release Tablets: An Overview with a Special Emphasis on Matrix Tablet," American Journal of Advanced Drug Delivery, 2017.
Brzeclo, W.,et al., "The Advent of a new Pseudoephedrine Product to Combat Methampetamine Abuse," Am J Drug Alcohol Abuse, 2013: 39(5): 284-290.
Extended European Search Report for Application No. 17173240.7 dated Nov. 28, 2017.
Jamini, M., et al, "Sustained Release Matrix Type Drug Delivery System: A Review," Journal of Drug Delivery & Therapeutics; 2012, 2(6), 142-148.
Kelly, C. et al, "Methamphetamine Synthesis Inhibition: Dissolving Metal Reductions," Johns Hopkins Univ. Applied Physics Lab., 2015, 1-10.
Misal, R, et al., "Matrix Tablet: A Promising Technique for Controlled Drug Delivery," Indo American Journal of Pharmaceutical Research, 2013.
Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis, 2018, 16-22.
Qi et al, "An Investigation into the Crystallisation Behavior of an Amorphous Cryomilled Pharmaceutical Material Above and Below the Glass Transition Temperature," Journal of Pharmaceutical Sciences, 2009, 196-208.
Patrick, K., et al., "Pharmacology of Methylphenidate, Amphetamine Enantiomers and Pemoline in Attention-Deficit Hyperactivity Disorder," Human Psychopharmacology, vol. 12, 527-546 (199).
Targin(R) Product Monograph. Purdue Pharma. Revised Mar. 1, 2016.
Low Substituted Hydroxypropyl Celluslose, Drugs.com, from https://www.drugs.com/inactive/low-substitute-hydroxypropyl-cellulose-581.html (2018).
Vezin, W. et al, "Adjustment of precompression force to reduce mixing-time dependence of tablet tensile strength," J. Pharm. Pharmacol. 1983, 35: 555-558 (Mar. 28, 1983).
Patel, et. al., "Poloxamers: A pharmaceutical excipient with therapeutic behaviors," PharmTech, vol. 1, No. 2, pp. 299-300 (Apr. 2009).
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re *Oxycontin Antitrust Litigation, Purdue Pharma LP* v. *Teva Pharmaceuticals*Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29th Annual Meeting of the Controlled Release Society, in collaboration with the Korea Society for Biomaterials, Minneapolis, 1st Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of The University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001—Crowley0000127 (2015).
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: Polyox(TM) WSR 30" (effective date: Sep. 18, 2001).

(56) References Cited

OTHER PUBLICATIONS

Dow, "Polyox Water-Soluble Resins: Degradation of Water-Soluble Resins," Technical Data (Oct. 2002).

Drug Bank "Oxymorphone," 2015; online, available at: www.dmgbank.ca/chugs/db01192 printed Jul. 1, 2015.

*Endo Pharmaceuticals Inc.* v. *Teva Pharmaceuticals USA, Inc.* (S.D.N.Y 2015)—Redacted Version.

FDA News Release, "FDA approves abuse-deterrent labeling for reformulated OxyContin," Apr. 16, 2013, available at http://www.fda.gov/NewsEvents/Newsroom/Press.Announcements/ucm348/252.htm.

FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.

Final Draft Labeling for Concerta Extended-Release Tablets Attachment to Approval Letter (2000); available at: http://www.accessdata.fda.gov/drugsatfda_docs/label/2000/21121lbl.pdf.

Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).

Griffith, D., "Potential new ADHD drug creating lots of big hopes," Sacramento Bee (California), Oct. 30, 2002.

Huang, H. et al,, "Preparation of Controlled Release Oral Dosage Forms by Low Temperature Melt Extrusion," AAPS PharmSci. 2000 2(S1).

Jaffe, S.L., "Failed Attempts At Intranasal Abuse of Concerta," Letters to the Editor, J. Am. Acad. Child Adolesc. Psychiatry 41:1 (Jan. 2002).

Jannsen Pharmaceuticals, Inc. CONCERTA Labeling Revisioins, Dec. 12, 2013; online, retrieved from: http://www.accessdata.fda.gov/dmgsatfda_docs/labeV2013/021121s032lbl.pdf.

Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GBMH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).

Kibbe, Coloring Agents, in Handbook of Pharmaceutical Excipients (3d ed. 2000).

Kidokoro, M. et al. ,"Properties of Tablets Containing Granulations of Ibuprofen and Acrylic Copolymers Prepared by Thermal Processes," Pharm Dev. and Tech. , 6:263-275 (2001).

Kinjo, N. et al, "Antiplasticization in the Slightly Plasticized Poly(vinyl chloride)," Polymer Journal 4(2):143-153 (1973).

Larhib, H. et al., "Compressing polyethyelene glycols: the effect of compression pressure and speed," Int 'l J Pharmaceutics (1997) 147: 199-205.

Lieberman, H., et al., Pharmaceutical Dosage Forms: Tablets, vol. 2, Ch. 5: Granulation Technology and Tablet Characterization (1990), Table of contents and 245-348.

Lyons et al., "Twitch Interpolation in the Assessment of the Maximum Force-Generating Capacity of the Jaw-Closing Muscles in Man," Arch. Oral. Biol. 41:12, 1161-1168 (1996).

Makki, A, et. al., Eds., A Dictionary of American Idioms, 4th Ed. Barron's, New York (2004), 342-343.

Markovitz, H., et al. "Calculations of Entanglement Coupling Spacings in Linear Polymers." Journal of Physical Chemistry, 1962. 66(8): 1567-1568.

McCrum, N., et al., Principles of Polymer Engineering. 2nd ed., New York: Oxford University Press. 447(199), Chapter 7, 296-351.

McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.

McQuay, H. et a. "Methods of Therapeutic Trials," Textbook of Pain 1125-1138 (P.D. Wall & R. Melzack eds., Elsevier 4th ed. 1999), Table of Contents and 1125-1138.

Miura et al., "Comparison of Maximum Bite Force and Dentate Status Between Healthy and Frail Elderly Persons," J. Oral Rehabilitation, vol. 28 (2001), pp. 592-595.

Miyagawa, Y. et al., "Controlled-release of diclofenac sodium from wax matrix granulate," Int 'l J. Pharmaceutics (1996) 138:215-224.

National Drug Intelligence Center Information Bulletin "OxyContin Diversion and Abuse" Jan. 2001.

Payne, H. et al., Denatonium Benzoate as a Bitter Aversive Additive in Ethylene Glycol and Methanol-Based Automotive Products, SAE Technical Paper 930589, Abstract (1993).

Pilpel, N., et al. "The effect of temperature on the tensile strength and disintegration of paracetamol and oxytetracylcine tablets," J Pharm Pharmac., 29:389-392 (1977).

Polyox Water-Soluble Resins NF in Pharmaceuticai-40.6iiions, Dow Chemical Company, Aug. 2002.

Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.

Rauwendaal, Chris, PhD, Responsive Expert Report of Chris Rauwendaal, Ph.D. Regarding Expert Report of Michael M. Crowley, Ph.D., dated Jul. 17, 2015.

Repka, M. et al. Pharmaceutical Applications of Hot-Melt Extrusion: Part II. Drug Dev. & Indus. Pharmacy (2007) 33:1043-1057.

Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

Seitz, J.A.; et al., "Evaluation of the Physical Properties of Compressed Tablets 1: Tablet Hardness and Friability," J. of Pharm. Sci. , 54:1353-1357 (1965).

Shah, et al., "Some Effects of Humidity and Heat on the Tableting Properties of Microcrystalline Cellulose Formulations 1," J. of Pharm. Sci., 57:181-182 (1967).

Singhal, et al., Handbook of Indices of Food Quality and Authenticity (1997), "Capsicum" p. 398-299.

Smith, K.L. et al. "High Molecular Weight Polymers of Ethylene Oxide—Plastic Properties." Industrial and Engineering Chemistry, 1958. 50(1): 12-16.

Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review,pdf.

Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Substance Abuse," Schizophrenia Bulletin, 23:215-228 (1997).

World Health Org., Cancer Pain Relief With a Guide to Opioid Availability (2d ed. 1996).

Yin, T.P., et al., "Viscoelastic Properties of Polyethylene Oxide in Rubber-Like State." Journal of Physical Chemistry, 1961. 65(3): 534-538.

Zacny, J. et al. Drug & Alcohol Dependence (2003) 69:215-232.

Zhang, F., "Hot-Melt Extrusion as a Novel Technology to Prepare Sustained-Release Dosage Forms," Dissertation University of Texas at Austin, Dec. 1999.

Sprockel, et. al, "A melt-extrusion process for manufacturing matrix drug delivery systems," Int. Journal of Pharmaceutic 155 (1997) 191-199.

BASF the chemical company, Kollicoat IR Technical information, Feb. 2013, p. 1-14 (2013).

Befort et al., "The Conserved Asparatate Residue in the Third Putative Transmember Domain," Molecular Pharmacology 1996: 49:216-223 (1996).

Domino E.F. (1991) Nicotine: A Unique Psychoactive Drug, In: Adlkofer F., Thurau K. (eds.) Effects of Nicotine on Biological Systems. APS Advances in Pharmacological Sciences. Birkhaeuser Basel (1991).

(56) References Cited

OTHER PUBLICATIONS

Fitzpatrick, J., "The influence of Superdisintegrants on Immediate Release," By Pharmaceutical Technology Editions [online] retrieved from http://www.pharmatech.com/influence-superdisintegrants-immediate-release; vol. 21, issue 6 (Jun. 1, 2011).

Kolar et al., "Treatmen of adults with attention-deficit/hyperactivity disorder," Neuropsychiatric Disease and Treatment 2008:4(3):389-403.

Rasmussen, N. "America's First Amphetamine Epidemic 1929-1971" American Journal of Public Health 2008:98(6): 974-985.

Suzuki, T, "Blood-brain barrier transport of opioid analgesics," Abstract, Yakugaki Zasshi; 131(10):1445-51 (2011).

Pintauro, Nicholas, D., Food Flavoring Processes, Table of Content. Park Ridge, NJ and London, UK, 1976.

European Pharmacopeia, 7th Ed. 2.2.8 and 2.2.10, 27ff. (2010).

Weinhold, et al. "Buprenorphine alone and in combination with naloxone in non-dependent humans." Drug & Alcohol Dependence 30.3 (1992): 263-274.

Ely et al., "Lithium-Ammonia Reduction of Ephedrine to Methamphetamine: An Unusual Clandestine Synthesis," Technical Note, 1990, 720-723.

Kunalan et al., "Investigation of the Reaction Impurities Associated with Methylamphetamine Synthesized using the Nagai Method," Anal. Chem. 2012, 84, 5744-52.

Lee et al., "Analysis of the impurities in the metamphetamine synthesized by thee different methods from ephedrine and pseudoephedrine," Forensic Science International 161 (2006), 209-215.

Person et al., Structural Determination of the Principal Byproduct of the Lithium-Ammonia Reduction Method of Methamphetamine Manufacture, J Forensic Sci, Jan. 2005, vol. 50, No. 1, 87-95.

Salouros et al., Isolation and Identification of Three By-Products Found in Methylamphetamine Synthesized by the Emde Route2010, 605-615.

Skinner, Harry F., "Methamphetamine Synthesis via Hydriodic Acid/Red Phosphorus Reduction of Ephedrine," Forensic Science International, 48 (1990), 123-134.

Polyox, 2004, online retrieved on Oct. 15, 2018.

Jedinger, N., et al., Eur. J. Pharm. Biopharm 87 (2014), 217-226.

U.S. Appl. No. 60/287,509, filed Dec. 22, 2002, Joshi et al.

U.S. Appl. No. 60/288,211, filed Sep. 2, 2004, Oshlack et al.

U.S. Appl. No. 60/310,514, filed Apr. 3, 2003, Oshlack et al.

U.S. Appl. No. 60/310.534, filed Apr. 10, 2004, Wright et al.

U.S. Appl. No. 60/376,470, filed Jan. 15, 2004, Ayer et al.

U.S. Appl. No. 60/384,442, filed Dec. 4, 2003, Fink et al.

De Brabander C., et al., "Development and evaluation of sustained release mini-matrices prepared via hot melt extrusion," Journal of Controlled Release 89 (2003), 235-247.

European Pharmacopoeia 3.0, 2.9.8 "Resistance to Crushing of Tablets", 1997, p. 135.

Goodman and Gilman, 1985, 7th edition, chapter 29, 674-715.

Houston, T.E., et al., "Bite Force and Bite Pressure: Comparison of Humans and Dogs," http://www.glapbta.com/BFBP.pdf, 2003, pp. 1-7.

King, Remington's Pharmaceutical Sciences 17th ed., Chapter 78, p. 1418-1419 (1985).

Pharma Tips ([online] retrieved on Mar. 22, 2018 from http://ww.pharmatips.in/Articles/Pharmaceutics/Tablet/Co-Processed-Directly-Compressed-Adjutants.aspx; May 2011: 10 pages).

Quadros, E. et al., "Evaluation of a novel colonic delivery device in vivo," STP Pharma Sci. 5, 77-82 (1995).

Sigma-Aldrich entry for CAS No. 9010-88-2; www.sigmaaldrich.com/catalog/product/aldrich/182249?lang=en&region=US (downloaded Jun. 2018).

Sumitomo Seika Chemicals, Co., Ltd, "Certificte of Analysis," Product: Polyethylene Oxide; Grade: PEO-18NF; Feb. 2, 2016.

Sumitomo Seika Chemicals, Co., Ltd, "Certificte of Analysis," Product: Polyethylene Oxide; Grade: PEO-20NF; Feb. 3, 2016.

Sumitomo Seika Chemicals, Co., Ltd, "Certificte of Analysis," Product: Polyethylene Oxide; Grade: PEO-20NF; Jan. 23, 2012.

Sumitomo Seika Chemicals, Co., Ltd, "Certificte of Analysis," Product: Polyethylene Oxide; Grade: PEO-20NF; May 15, 2013.

Theeuwes, Felix et al., Osmotic Systems for Colon-Targeted Drug Delivery in Colonic Drug Absorption and Metabolism (Peter R. Bieck ed., 1993).

Turkington, R., "Amphetamines," in Chemicals used for Illegal Purposes. A Guide for first Responders to Identify Explosives, Recreational Drugs, and Poisons, 2010, p. 247.

Wooten, Marvin R. et al., Intracerebral Hemorrhage and Vasculitis Related to Ephedrine Abuse, 13 Annals of Neurology 337 (1983).

Evekeo, (Amphetame Sulfate) for treating patients with ADHD website [online] https://www.evekeo.com.about-evekeo; 2019:5 pages), 2019.

Lurie et al., "Chiral Resolution of Cationic Drugs of Forensic Interest," (Analytical Chemistry 1994; 66(22): 4019-4026.

Claffey et al, "Amphetamine Adducts of Melanin Intermediates Demonstrated by Matrix-Assisted Laser Desorption Ionization Time-of-Flight Mass Spectrometry," Chem. Res. Toxicol. 2001, 14, 1339-1344.

Evans, J.C, et al. "Optical tocopherol concentrations to inhibit soybean oil oxidation," Journal of The American Oil Chemists' Society 79.1 (2002): 47-51.

Quinn, M.E. "Alpha Tocopherol" in Handbook of Pharmaceuical Excipients, Sixth Edition (2009), 31-33.

ABUSE-PROOFED DOSAGE FORM

This application is a continuation of U.S. patent application Ser. No. 15/587,501, filed May 5, 2017, which is a continuation of U.S. patent application Ser. No. 15/245,424, filed Aug. 24, 2016; now U.S. Pat. No. 9,675,610; which is a continuation of U.S. patent application Ser. No. 14/527,911, filed Oct. 30, 2014, abandoned, which is a continuation of U.S. patent application Ser. No. 14/069,439, filed Nov. 1, 2013, abandoned, which is a continuation of U.S. patent application Ser. No. 13/803,789, filed Mar. 14, 2013, abandoned, which is a continuation of U.S. patent application Ser. No. 13/572,926, filed Aug. 13, 2012, abandoned, which is a continuation of Ser. No. 13/365,742, filed Feb. 3, 2012, abandoned, which is a continuation of U.S. patent application Ser. No. 12/822,719, filed Jun. 24, 2010, abandoned, which is a divisional of U.S. patent application Ser. No. 11/007,887, filed Dec. 9, 2004, now U.S. Pat. No. 7,776,314, which is a continuation-in-part of International Patent Application No. PCT/EP2003/006314, filed Jun. 16, 2003, which claims foreign priority benefit under 35 U.S.C. § 119 of the German Patent Applications Nos. 102 50 083.5, filed Oct. 25, 2002, and 102 27 077.5, filed Jun. 17, 2002, the entire disclosures of which patent applications are incorporated herein by reference.

The present invention relates to a solid dosage form with reduced parenteral abuse containing, in addition to one or more active ingredients with potential for abuse, at least one viscosity-increasing agent in quantities such that, on extraction with the assistance of a necessary minimum quantity of aqueous liquid, a gel is formed which can still preferably pass through a needle, which gel, however, remains visually distinguishable even after being introduced into a further quantity of an aqueous liquid.

Many pharmaceutical active ingredients, in addition to having excellent activity in their appropriate application, also have potential for abuse, i.e. they can be used by an abuser to bring about effects other than those intended. Opiates, for example, which are highly active in combating severe to very severe pain, are frequently used by abusers to induce a state of narcosis or euphoria.

Dosage forms which contain active ingredients with potential for abuse, even when taken orally in an abusively large quantity, do not usually give rise to the result desired by the abuser, namely a rapid rush or "kick", because blood levels of the active ingredients increase only slowly. In order nevertheless to achieve the desired effects and enable abuse, the corresponding dosage forms are comminuted, for example ground, by the abuser and the active ingredient is extracted from the powder obtained by comminution of the dosage form with the assistance of a preferably aqueous liquid, preferably the minimum quantity necessary, and the resultant solution, optionally after filtration through cotton wool or cellulose wadding, is administered parenterally, in particular intravenously. Due to this parenteral administration, only the smallest possible quantities of an aqueous liquid are used for extraction, in particular so as to obtain the smallest possible injection volume with active ingredient which results in the desired rapid rush or "kick". In this manner, parenteral administration, in comparison with oral administration, tends to give rise to an accelerated rise in levels of the active ingredient providing the abuser with the desired result.

In order to prevent this form of abuse, it has been proposed in U.S. Pat. No. 4,070,494 to prevent the extraction of an active ingredient from a dosage form by the addition of a swellable agent. On addition of water, this agent swells and ensures that only a small quantity of active ingredient containing liquid is obtained which can be administered parenterally by the abuser. The majority of this dosage form which has swollen is cannot be administered.

A corresponding approach to the prevention of parenteral abuse also underlies the multilayer tablet disclosed in WO 95/20947 which contains the active ingredient with potential for abuse and one or more gel formers each in different layers.

According to this prior art teaching, the viscosity-increasing agents are added in quantities such that the corresponding gel cannot be administered with the assistance of conventional hypodermic needles.

The object of the present invention was to provide a dosage form with at least reduced potential for abuse for active ingredients having with such potential, which dosage form prevents any preferably still possible parenteral, in particular intravenous, abuse of the active ingredients.

This object has been achieved by the provision of the solid dosage form according to the invention with at least reduced potential for parenteral abuse, which dosage form, in addition to one or more active ingredients with potential for abuse, comprises at least one viscosity-increasing agent in a quantity such that a gel which may preferably still pass through a needle is formed in an extract obtained from the dosage form with the assistance of a necessary minimum quantity of an aqueous liquid, which gel remains visually distinguishable when introduced into a further quantity of an aqueous liquid.

For the purposes of the present invention, visually distinguishable means that the active ingredient-containing gel formed by extraction from the dosage form with the assistance of a necessary minimum quantity of aqueous liquid, when introduced with a hypodermic needle with a diameter of 0.9 mm into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 min.

The increase in viscosity of the gel with the assistance of the selected viscosity-increasing agent means that, although this has been rendered more difficult, the gel may still be passed through a needle or injected. It also means that when the resultant extract or gel is introduced at 37° C. into a further quantity of aqueous liquid, for example also by injection into blood, a largely cohesive thread is initially obtained which, while it may be broken up into smaller fragments by mechanical action, it cannot be dispersed or even dissolved in such a manner that it may safely be administered parenterally, in particular intravenously.

Intravenous administration of such an extract would most probably result in obstruction of blood vessels, associated with serious embolism or even death of the abuser.

For the purposes of the present invention, an extract or gel obtained from the dosage form according to the invention with the assistance of a necessary minimum quantity of an aqueous liquid, preferably water, is deemed to be passable through a needle if the gel formed in this manner can still be drawn up and injected back out of a hypodermic needle with a diameter of 2 mm, preferably of 1.5 mm, particularly preferably of 0.6 mm. Pharmaceutical active ingredients with potential for abuse are known to the person skilled in the art, as are the quantities thereof to be used and processes for the production thereof, and may be present in the dosage form according to the invention as such, in the form of corresponding derivatives, in particular esters or ethers, or in each case in the form of corresponding physiologically acceptable compounds, in particular in the form of the salts or solvates thereof. The dosage form according to the invention is also suitable for the administration of a plurality of active ingredients. It is preferably used for the administration of a single active ingredient.

The present invention, thus, relates in one embodiment to a method of treating a disease or disorder in a patient in need of such treatment, said disease or disorder being treatable with one or more active ingredients with potential for abuse, wherein said one or more active ingredients with potential for abuse are selected from the group consisting of opiates, opioids, tranquilizers, stimulants and narcotics, said method comprising administering to said patient the dosage form according to the present invention, wherein said dosage form comprises one or more of said active ingredients effective to treat said disease or disorder.

The dosage form according to the invention is in particular suitable for preventing abuse of a pharmaceutical active ingredient selected from the group consisting of opiates, opioids, tranquillisers, preferably benzodiazepines, stimulants and other narcotics.

The dosage form according to the invention is very particularly preferably suitable for preventing abuse of an opiate, opioid, tranquilliser or another narcotic, which is selected from the group consisting of N-{1-[2-(4-Ethyl-5-oxo-2-tetrazolin-1-yl)ethyl]-4-methoxymethyl-4-piperidyl}propionanilide (alfentanil), 5,5-diallylbarbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methylphenethylamine (amphetamine), 2-(α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-6H-thieno[3,2-f][1,2,4]triazolo[4,3-a][1,4]diazepine (brotizolam), 17-cyclopropylmethyl-4,5α-epoxy-7α[(S)-1-hydroxy-1,2,2-trimethylpropyl]-6-methoxy-6,14-endo-ethanomorphinan-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepin-3-yl) dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine 4-oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one (clotiazepam), 10-chloro-11b-(2-chlorophenyl)-2,3,7,11b-tetrahydrooxazolo[3,2-d][1,4]benzodiazepin-6(5H)-one (cloxazolam), (−)-methyl-[3β-benzoyloxy-2β(1αH,5αH)-tropane carboxylate] (cocaine), 4,5α-epoxy-3-methoxy-17-methyl-7-morphinen-6α-ol (codeine), 5-(1-cyclohexenyl)-5-ethyl barbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphene), dezocine, diampromide, diamorphone, 7-chloro-7-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6α-morphinandiol (dihydromorphine), dimenoxadol, dimephetamol, dimethylthiambutene, dioxaphetyl butyrate, dipipanone, (6aR,10aR)-6,6,9-trimethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-(a)][1,4]benzodiazepine (estazolam), ethoheptazine, ethylmethylthiambutene, ethyl [7-chloro-5-(2-fluorophenyl)-2,3-dihydro-2-oxo-1H-1,4-benzodiazepine-3-carboxylate] (ethyl loflazepate), 4,5α-epoxy-3-ethoxy-17-methyl-7-morphinen-6α-ol (ethylmorphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorboman-2-ylamine (fencamfamine), 7-[2-(α-methylphenethylamino)ethyl]-theophylline) (fenethylline), 3-(α-methylphenethylamino) propionitrile (fenproporex), N-(1-phenethyl-4-piperidyl) propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolyl[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethylmorphinan, 11-chloro-8,12b-dihydro-2,8-dimethyl-12b-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenyl-heptan-3-ylacetate (levacetylmethadol (LAAM)), (−)-6-dimethylamino-4,4-diphenol-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a][1,4]-benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylene dicarbamate (meprobamate), meptazinol, metazocine, methylmorphine, N,α-dimethylphenethylamine (metamphetamine), (±)-6-dimethylamino-4,4-diphenol-3-heptanone (methadone), 2-methyl-3-o-tolyl-4(3H)-quinazolinone (methaqualone), methyl [2-phenyl-2-(2-piperidyl)acetate] (methylphenidate), 5-ethyl-1-methyl-5-phenylbarbituric acid (methylphenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl)acetamide (modafinil), 4,5α-epoxy-17-methyl-7-morphinen-3,6α-diol (morphine), myrophine, (±)-trans-3-(1,1-dimethylheptyl)-7,8,10,10α-tetrahydro-1-hydroxy-6,6-dimethyl-6H-dibenzo-[b,d]pyran-9(6αH)-one (nabilone), nalbuphene, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2(3H)-one (nordazepam), norlevorphanol, 6-dimethylamino-4,4-diphenyl-3-hexanone (normethadone), normorphine, norpipanone, the exudation from plants belonging to the species *Papaver somniferum* (opium), 7-chloro-3-hydroxy-5-phenyl-1H-1,4-benzodiazepin-2 (3H)-one (oxazepam), (cis-trans)-10-chloro-2,3,7,11b-tetrahydro-2-methyl-11b-phenyloxazolo[3,2-d][1,4]benzodiazepin-6-(5H)-one (oxazolam), 4,5α-epoxy-14-hydroxy-3-methoxy-17-methyl-6-morphinanone (oxycodone), oxymorphone, plants and parts of plants belonging to the species *Papaver somniferum* (including the subspecies *setigerum*) (*Papaver somniferum*), papaveretum, 2-imino-5-phenyl-4-oxazolidinone (pemoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl-(1-methyl-4-phenyl-4-piperidinecarboxylate) (pethidine), phenadoxone, phenomorphane, phenazocine, phenoperidine, piminodine, pholcodeine, 3-methyl-2-phenylmorpholine (phenmetrazine), 5-ethyl-5-phenylbarbituric acid (phenobarbital), α,α-dimethylphenethylamine (phentermine), 7-chloro-5-phenyl-1-(2-propynyl)-1H-1,4-benzodiazepin-2(3H)-one (pinazepam), α-(2-piperidyl)benzhydryl alcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl)propionamide, methyl {3-[4-methoxycarbonyl-4-(N-phenylpropanamido)piperidino]propanoate} (remifentanil), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl)ethyl]-4-piperidyl}propionanilide (sufentanil), 7-chloro-2-hydroxymethyl-5-phenyl-1H-1,4-benzodiazepin-2(3H)-one (temazepam), 7-chloro-5-(1-cyclohexenyl)-1-methyl-1H-1,4-benzodiazepin-2(3H)-one (tetrazepam), ethyl (2-dimethylamino-1-phenyl-3-cyclohexene-1-carboxylate) (tilidine, cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R*,2R*)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl) cyclohexanol and for corresponding stereoisomeric compounds, the corresponding derivatives thereof in each case, in particular esters or ethers, and the physiologically acceptable compounds thereof in each case, in particular the salts and solvates thereof.

The compounds (1R*,2R*)-3-(3-dimethylamino-1-ethyl-2-methyl-propyl)-phenol and (1R,2R,4S)-2-(dimethylamino)methyl-4-(p-fluorobenzyloxy)-1-(m-methoxyphenyl)cyclohexanol, the physiologically acceptable compounds thereof, in particular the hydrochlorides thereof and processes for the production thereof are respectively known, for example, from EP-A-693475 and EP-A-780369. The corresponding descriptions are hereby introduced as a reference and are deemed to be part of the disclosure.

In order to verify whether a viscosity-increasing agent is suitable for use in the dosage form according to the invention, said agent is first formulated in a corresponding dosage form in quantities such that there is no appreciable (±5%) influence on active ingredient release relative to a dosage form without viscosity-increasing agent. The corresponding dosage form is moreover comminuted, preferably ground, and extracted with 10 ml water at 25° C. If a gel is furthermore formed which meets the above-stated conditions, the corresponding viscosity-increasing agent is suitable for the production of a dosage form according to the invention.

Preferably, one or more viscosity-increasing agents are used in the dosage form according to the invention, said agents being selected from the group consisting of microcrystalline cellulose with 11 wt. % carboxymethylcellulose sodium (Avicel® RC 591), carboxymethylcellulose sodium (Blanose®, CMC-Na C3001P®, Frimulsion BLC-5®, Tylose C300 P®), polyacrylic acid (Carbopol® 980 NF, Carbopol® 981), locust bean flour (Cesagum® LA-200, Cesagum® LID/150, Cesagum® LN-1), pectins, preferably from citrus fruits or apples (Cesapectin® HM Medium Rapid Set), waxy maize starch (C*Gel 04201®), sodium alginate (Frimulsion ALG (E401)®), guar flour (Frimulsion BM®, Polygum 2611-75®), iota-carrageenan (Frimulsion D021®), karaya gum, gellan gum (Kelcogel F®, Kelcogel LT100®), galactomannan (Meyprogat 150®), tara stone flour (Polygum 4311®), propylene glycol alginate (Protanal-Ester SD-LB®), sodium hyaluronate, tragacanth, tara gum (Vidogum SP 200®), fermented polysaccharide welan gum (K1A96), xanthans such as xanthan gum (Xantural 180®). The names stated in brackets are the trade names by which the materials are known commercially.

In general, a quantity of 0.1 to 25 wt. %, preferably of 0.5 to 15 wt. %, particularly preferably of 1-10 wt. % of the viscosity-increasing agent, relative to the total formulation, is sufficient in order to meet the above-stated conditions.

The viscosity-increasing agents are preferably present in the dosage form according to the invention in quantities of ≥5 mg, particularly preferably of ≥10 mg per dosage form, i.e. per administration unit.

In a particularly preferred embodiment of the present invention, the viscosity-increasing agents used are those which, in addition to the above-stated conditions, also form a gel which encloses air bubbles on extraction from the dosage form with the necessary minimum quantity of aqueous liquid. The resultant gels are distinguished by a turbid appearance, which provides the potential abuser with an additional optical warning and discourages him/her from administering the gel parenterally.

The active ingredient or ingredients with potential for abuse and the viscosity-increasing agents and optionally physiologically acceptable auxiliary substances may be formulated to yield the dosage form according to the invention in accordance with conventional methods known to the person skilled in the art. Corresponding methods for formulating the dosage form according to the invention are known per se to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

Surprisingly, due to the inventive selection of the viscosity-increasing agents, it is possible to combine the active ingredients and the viscosity-increasing agents in the dosage form according to the invention without spatial separation from one another, without there being any impairment of release of the active ingredient from the correctly administered dosage form relative to a corresponding dosage form which does not comprise the viscosity-increasing agent.

Obviously, however, it is also possible to combine the viscosity-increasing agents and the active ingredients in the dosage form in a mutually spatially separated arrangement.

The parenteral abuse-proofed solid dosage forms according to the invention are preferably suitable for oral or rectal administration, particularly preferably for oral administration.

Where the dosage form according to the invention is intended for rectal administration, it preferably assumes the form of a suppository.

If the dosage form according to the invention is intended for oral administration, it preferably assumes the form of a tablet, a capsule or of an oral osmotic therapeutic system (OROS).

Oral osmotic therapeutic systems and suitable materials and processes for the production thereof are known per se to the person skilled in the art, for example from U.S. Pat. Nos. 4,612,008, 4,765,989 and 4,783,337. The corresponding descriptions are hereby introduced as a reference and are deemed to be part of the disclosure.

The corresponding oral osmotic therapeutic system may preferably assume the form of a single or twin chamber system, in each case with a single layer or multilayer structure. In these systems, the push layer, i.e. the layer which produces the osmotic pressure by swelling, by means of which the overlying layer is expelled from the system, preferably at least in part consists of the viscosity-increasing agents used according to the invention.

In a further preferred embodiment of the present invention, the orally administrable dosage form according to the invention assumes multiparticulate form containing in each case the complete mixture of active ingredient and viscosity-increasing agent, preferably in the form of microtablets, microcapsules, micropellets, granules, spheroids, beads or pellets, preferably packaged in capsules or press-moulded into tablets The multiparticulate forms preferably have a size in the range from 0.1 to 3 mm, particularly preferably in the range from 0.5 to 2 mm.

The dosage form according to the invention may preferably also comprise one or more active ingredients, blended with the viscosity-increasing agent, at least in part in delayed-release form, wherein delayed release may be achieved with the assistance of conventional materials and processes known to the person skilled in the art, for example by embedding the active ingredient in a delayed-release matrix or by applying one or more delayed-release coatings.

Delayed release of the active ingredient may preferably also be achieved by purposeful selection of one or more of the above-stated viscosity-increasing agents in suitable quantities as the matrix material. The person skilled in the art may determine the agents and the quantity thereof suitable for the particular desired release by simple preliminary testing, wherein it must, of course, be ensured that, as described above, gel formation occurs when the attempt is made to abuse the resultant dosage form.

In any event, it must be ensured that the delayed-release auxiliary substances, and likewise further optionally present auxiliary substances, do not interfere with gel formation or impair the stability of the gel which is formed.

If the dosage form according to the invention is intended for oral administration, it may also comprise a coating which is resistant to gastric juices and dissolves as a function of the pH value of the release environment.

By means of this coating, it is possible to ensure that, when correctly administered, the dosage form according to the invention passes through the stomach undissolved and the active ingredient is only released in the intestines. The coating which is resistant to gastric juices preferably dissolves at a pH value of between 5 and 7.5.

Corresponding materials and methods for the controlled release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

In a further preferred embodiment, the dosage form according to the invention contains the active ingredient not only in its delayed-release form, but also in its non-delayed-release form. By combination with the immediately released active ingredient, it is possible to obtain an initial dose for rapid pain relief. The slow release from the delayed-release form then prevents any rapid decline in action.

The invention is explained below with reference to Examples. These explanations are given merely by way of example and do not restrict the general concept of the invention.

EXAMPLES

Example 1

Matrix tablets with the following composition per tablet

| | |
|---|---|
| (−)-(1R,2R)-3-(3-Dimethylamino-1-ethyl-2-methyl-propyl)phenol hydrochloride | 100 mg |
| Hydroxypropylmethylcellulose (Metolose 90 SH 100,000 from Shinetsu), 100,000 mPa · s | 70 mg |
| Xanthan, NF | 10 mg |
| Microcrystalline cellulose (Avicel PH 102 from FMC) | 123 mg |
| Highly disperse silicon dioxide | 4 mg |
| Magnesium stearate | 3 mg |
| Total quantity | 310 mg | were produced in the following manner in a batch size of 1000 tablets: All the constituents were weighed out and screened in Quadro Comil U10 screening machine using a screen size of 0.813 mm, mixed in a container mixer (Bohle LM 40) for 15 min±15 s at a rotational speed of 20±1 rpm and pressed on a Korsch EKO eccentric press to form biconvex tablets with a diameter of 10 mm, a radius of curvature of 8 mm and an average tablet weight of 310 mg.

In vitro release was determined using the Ph. Eur. paddle method at 75 rpm in 900 ml of pH 6.8 buffer to Ph. Eur. at 37° C., with detection by UV spectrometry, and is shown in the following Table, together with a comparison with a corresponding tablet with 80 mg of hydroxypropylmethylcellulose ("HPMC") without addition of xanthan.

| Time [min] | Total quantity of active ingredient released [%] from tablets according to Example 1 (70 mg HPMC + 10 mg xanthan) | Total quantity of active ingredient released [%] from tablets with 80 mg HPMC (without xanthan) |
|---|---|---|
| 0 | 0 | 0 |
| 30 | 19 | 18 |
| 240 | 62 | 59 |
| 480 | 83 | 80 |
| 600 | 88 | 87 |
| 720 | 93 | 93 |

One of the tablets containing xanthan was ground and shaken with 10 ml of water. A viscous, turbid suspension formed. Once the coarse, solid components of the suspension had settled out, the gel which had formed was drawn up into a syringe with a 0.9 mm diameter needle. The drawn up gel was injected into water at 37° C. and threads, which did not mix with the water, with the diameter of the needle remained clearly discernible While the threads could be broken up by stirring, they could not be dissolved and the thread fragments remained visible to the naked eye. Were such an extract to be injected into blood vessels, vessel blockages would occur.

Example 2 (Comparative Example Regarding Very Poor Needle Passage Properties)

Matrix tablets with the following composition per tablet

| | |
|---|---|
| (−)-(1R,2R)-3-(3-Dimethylamino-1-ethyl-2-methyl-propyl)phenol hydrochloride | 100 mg |
| Hydroxypropylmethylcellulose (Metolose 90 SH 100,000 from Shinetsu), 100,000 mPa · s | 40 mg |
| Xanthan, NF | 40 mg |
| Microcrystalline cellulose (Avicel PH 102 from FMC) | 123 mg |
| Highly disperse silicon dioxide | 4 mg |
| Magnesium stearate | 3 mg |
| Total quantity | 310 mg | were produced as stated in Example 1 and their release characteristics were investigated.

| Time [min] | Total quantity of active ingredient released [%] |
|---|---|
| 0 | 0 |
| 30 | 19 |
| 240 | 61 |
| 480 | 81 |
| 600 | 87 |
| 720 | 91 |

One of the tablets was ground and shaken with 10 ml of water. A viscous, turbid suspension with enclosed air bubbles formed, the viscosity of which was greater than in Example 1. Once the coarse, solid components of the suspension had settled out, the gel which had formed was drawn up into a syringe with a 0.9 mm diameter needle. The drawn up gel was injected into water at 37° C. and threads, which did not mix with the water, with the diameter of the needle were clearly discernible. While the threads could be broken up by stirring, they could not be dissolved and the thread fragments remained visible to the naked eye. Were such a gel to be injected into blood vessels, vessel blockages would occur.

Example 3

Matrix tablets with the following composition per tablet

| | |
|---|---|
| (−)-(1R,2R)-3-(3-dimethylamino-1-ethyl-2-methyl-propyl)phenol hydrochloride | 100 mg |
| Xanthan, NF | 80 mg |
| Microcrystalline cellulose (Avicel PH 102 from FMC) | 123 mg |
| Highly disperse silicon dioxide | 4 mg |
| Magnesium stearate | 3 mg |
| Total quantity | 310 mg | were produced as stated in Example 1.

One of these tablets was ground and shaken with 10 ml of water. A viscous, turbid suspension, which had enclosed air bubbles, formed, the viscosity of which was higher than in Example 1. Once the coarse, solid components of the suspension had settled out, the gel which had formed was drawn up into a syringe with a 0.9 mm diameter needle. The drawn up gel was injected into water at 37° C. and clearly discernible threads, which did not mix with the water, with the diameter of the needle were visible. While the threads could be broken up by stirring, they could not be dissolved and the thread fragments remained visible to the naked eye. Were such a gel to be injected into blood vessels, vessel blockages would occur.

Examples 4-7

Matrix tablets with the following composition per tablet

| Example | 4 | 5 | 6 | 7 |
|---|---|---|---|---|
| (−)-(1R,2R)-3-(3-Dimethylamino-1-ethyl-2-methyl-propyl)phenol hydrochloride | 100 mg | 100 mg | 100 mg | 100 mg |
| Hydroxypropylmethyl-cellulose (Metolose 90 SH 100,000 from Shinetsu), 100,000 mPa · s | 80 mg | 80 mg | 80 mg | 80 mg |
| Carboxymethylcellulose (Tylose C300) | 10 mg | | | |
| Carboxymethylcellulose (Tylose C600) | | 10 mg | | |
| Hydroxyethylcellulose (Tylose H300) | | | 10 mg | |
| Hydroxyethylcellulose (Tylose H4000) | | | | 10 mg |
| Microcrystalline cellulose (Avicel PH 102 from FMC) | 123 mg | 123 mg | 123 mg | 123 mg |
| Highly disperse silicon dioxide | 4 mg | 4 mg | 4 mg | 4 mg |
| Magnesium stearate | 3 mg | 3 mg | 3 mg | 3 mg |
| Total quantity | 320 mg | 320 mg | 320 mg | 320 mg | were produced as stated in Example 1.

One of each of these tablets was ground and shaken with 10 ml of water. A viscous, turbid suspension with enclosed air bubbles formed. Once the coarse, solid components of the suspension had settled out, the [gel] was drawn up into a syringe with a 0.9 mm diameter needle. The drawn up gel was injected into water at 37° C. and clearly visible threads, which did not mix with the water, with the diameter of the needle remained discernible. While the threads could be broken up by stirring, they could not be dissolved and the thread fragments remained visible to the naked eye. Were such a gel to be injected into blood vessels, vessel blockages would occur.

Examples 8-13

Matrix tablets with the following composition per tablet

| | Example | | | | | |
|---|---|---|---|---|---|---|
| | 8 | 9 | 10 | 11 | 12 | 13 |
| Morphine sulfate pentahydrate | 60 mg | 60 mg | 60 mg | 60 mg | 60 mg | 60 mg |
| Hydroxypropylmethylcellulose (Metolose 90 SH 15,000 from Shinetsu), 15,000 mPa · s | 60 mg | 60 mg | 60 mg | 60 mg | 60 mg | 60 mg |
| Xanthan, NF | 10 mg | 30 mg | | | | |
| Carboxymethylcellulose (Tylose C300) | | | 10 mg | | | |
| Carboxymethylcellulose (Tylose C600) | | | | 10 mg | | |
| Hydroxyethylcellulose (Tylose H300) | | | | | 10 mg | |
| Hydroxyethylcellulose (Tylose H4000) | | | | | | 10 mg |
| Microcrystalline cellulose (Avicel PH 102 from FMC) | 123 mg | 123 mg | 123 mg | 123 mg | 123 mg | 123 mg |
| Highly disperse silicon dioxide | 4 mg | 4 mg | 4 mg | 4 mg | 4 mg | 4 mg |
| Magnesium stearate | 3 mg | 3 mg | 3 mg | 3 mg | 3 mg | 3 mg |

One of each of these tablets was ground and shaken with 10 ml of water. A viscous, turbid suspension with enclosed air bubbles formed. Once the coarse, solid components of the suspension had settled out, the [gel] was drawn up into a syringe with a 0.9 mm diameter needle. The drawn up gel was injected into water at 37° C. and clearly visible threads, which did not mix with the water, with the diameter of the needle remained discernible. While the threads could be broken up by stirring, they could not be dissolved and the thread fragments remained visible to the naked eye. Were such a gel to be injected into blood vessels, vessel blockages would occur.

Examples 14-18

Capsules with the following composition of the simple powder mixture per capsule (size 4 capsule)

| Example | 14 | 15 | 16 | 17 | 18 |
|---|---|---|---|---|---|
| Morphine sulfate pentahydrate | 20 mg | 20 mg | 20 mg | 20 mg | 20 mg |
| Xanthan, NF | 10 mg | | | | |
| Carboxymethylcellulose (Tylose C300) | | 10 mg | | | |
| Carboxymethylcellulose (Tylose C600) | | | 10 mg | | |
| Hydroxyethylcellulose (Tylose H300) | | | | 10 mg | |
| Hydroxyethylcellulose (Tylose H4000) | | | | | 10 mg |
| Microcrystalline cellulose (Avicel PH 102 from FMC) | 68 mg | 68 mg | 68 mg | 68 mg | 68 mg |
| Highly disperse silicon dioxide | 1 mg | 1 mg | 1 mg | 1 mg | 1 mg |
| Magnesium stearate | 1 mg | 1 mg | 1 mg | 1 mg | 1 mg |

One of each of these tablets was ground and shaken with 10 ml of water. A viscous, turbid suspension with enclosed air bubbles formed. Once the coarse, solid components of the suspension had settled out, the [gel] was drawn up into a syringe with a 0.9 mm diameter needle. The drawn up gel was injected into water at 37° C. and clearly visible threads, which did not mix with the water, with the diameter of the needle remained discernible. While the threads could be broken up by stirring, they could not be dissolved and the thread fragments remained visible to the naked eye. Were such a gel to be injected into blood vessels, vessel blockages would occur.

The invention claimed is:
1. A tablet for oral administration with reduced potential for parenteral abuse, said tablet comprising:
 (a) one or more active ingredients having potential for abuse selected from the group consisting of hydrocodone, morphine, oxycodone, tramadol, and pharmaceutically acceptable salts and solvates thereof; and
 (b) at least one viscosity-increasing agent in a quantity such that an aqueous extract of a total content of the tablet when comminuted and combined with 10 ml of water at 25° C. forms a gel that can be drawn up into and injected back out of a hypodermic needle having a diameter of 0.9 mm, into a further quantity of water, wherein threads of the gel injected from said needle remain visible to the naked eye in said further quantity of water at 37° C.
2. The tablet according to claim 1, wherein the active ingredient is oxycodone or a salt or solvate thereof.
3. The tablet according to claim 1, wherein the active ingredient is hydrocodone or a salt or solvate thereof.
4. The tablet according to claim 1, wherein the active ingredient is morphine or a salt or solvate thereof.
5. The tablet according to claim 1, wherein the one or more viscosity-increasing agents are selected from the group consisting of microcrystalline cellulose with 11 wt. % carboxymethylcellulose sodium, carboxymethylcellulose sodium, polyacrylic acid, locust bean flour, citrus pectin, waxy maize starch, sodium alginate, guar flour, iota-carrageenan, karaya gum, gellan gum, galactomannan, tara stone flour, propylene glycol alginate, apple pectin, lemon peel pectin, sodium hyaluronate, tragacanth, tara gum, fermented polysaccharide welan gum and xanthan gum.
6. The tablet according to claim 1, comprising at least one active ingredient in controlled release form.
7. The tablet according to claim 1, comprising a coating resistant to gastric juices.

8. The tablet according to claim 1, in multiparticulate form, wherein said multiparticulate form is in the form of microtablets, microcapsules, micropellets, granules, spheroids, beads or pellets, packaged in capsules or press-molded into tablets.

9. The tablet according to claim 1, wherein said threads remain visible to the naked eye in said further quantity of water for at least one minute.

10. The tablet according to claim 1, wherein said threads remain visible to the naked eye in said further quantity of water for at least ten minutes.

11. The tablet according to claim 1, which further comprises microcrystalline cellulose.

12. The tablet according to claim 1, which further comprises hydroxypropylmethylcellulose.

13. A solid dosage form for oral administration with reduced potential for parenteral abuse, said dosage form comprising:
(a) one or more active ingredients having potential for abuse selected from the group consisting of hydrocodone, morphine, oxycodone, tramadol, and pharmaceutically acceptable salts and solvates thereof; and
(b) one or more viscosity-increasing components, in a total quantity, for all said components combined, that is equal to or greater than 5 mg per dosage form, that quantity being selected such that an aqueous extract of a total content of the dosage form, when comminuted and combined with 10 ml of water at 25° C., forms a gel that is capable of being drawn into and then expelled from a hypodermic needle having a diameter of 0.9 mm, wherein threads of said gel, formed upon exit from said needle into a further quantity of water at 37° C., remain visible to the naked eye.

14. The dosage form according to claim 13, wherein the active ingredient is oxycodone or a salt or solvate thereof.

15. The dosage form according to claim 13, wherein the active ingredient is hydrocodone or a salt or solvate thereof.

16. The dosage form according to claim 13, wherein the active ingredient is morphine or a salt or solvate thereof.

17. The dosage form according to claim 13, wherein said threads remain visible to the naked eye in said further quantity of water for at least one minute.

18. The dosage form according to claim 13, wherein said threads remain visible to the naked eye in said further quantity of water for at least ten minutes.

19. The dosage form according to claim 13, comprising at least one active ingredient in controlled release form.

20. The dosage form according to claim 13, which further comprises microcrystalline cellulose.

21. The dosage form according to claim 13, which further comprises hydroxypropylmethylcellulose.

22. A tablet for oral administration with reduced potential for parenteral abuse, said tablet comprising:
(a) one or more active ingredients with potential for abuse selected from the group consisting of hydrocodone, morphine, oxycodone, tramadol and pharmaceutically acceptable salts and/or solvates thereof; and
(b) one or more viscosity-increasing agents;
wherein the tablet when its total content is comminuted and combined with 10 ml of water at 25° C. forms an injectable gel that can be drawn up into and injected back out of a syringe having a diameter of 0.9 mm, but wherein the injectable gel cannot be safely injected from said syringe into a blood vessel of an abuser because the presence of the injectable gel in the abuser's blood vessels would obstruct one or more of said abuser's blood vessels.

23. The tablet according to claim 22, wherein the active ingredient is oxycodone or a salt or solvate thereof.

24. The tablet according to claim 22, wherein the active ingredient is hydrocodone or a salt or solvate thereof.

25. The tablet according to claim 22, wherein the active ingredient is morphine or a salt or solvate thereof.

26. The tablet according to claim 22, which further comprises microcrystalline cellulose.

27. The tablet according to claim 22, which further comprises hydroxypropylmethylcellulose.

28. The tablet according to claim 22, comprising at least one active ingredient in controlled release form.

* * * * *